United States Patent
Perschbacher et al.

(10) Patent No.: US 10,702,180 B2
(45) Date of Patent: Jul. 7, 2020

(54) ATRIAL FIBRILLATION DISCRIMINATION USING HEART RATE CLUSTERING

(71) Applicant: Cardiac Pacemakers, Inc., St. Paul, MN (US)

(72) Inventors: David L. Perschbacher, Coon Rapids, MN (US); Sunipa Saha, Shoreview, MN (US); Deepa Mahajan, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 249 days.

(21) Appl. No.: 15/864,953

(22) Filed: Jan. 8, 2018

(65) Prior Publication Data

US 2018/0192902 A1 Jul. 12, 2018

Related U.S. Application Data

(60) Provisional application No. 62/444,046, filed on Jan. 9, 2017.

(51) Int. Cl.
| | |
|---|---|
| *A61B 5/04* | (2006.01) |
| *A61B 5/046* | (2006.01) |
| *A61B 5/00* | (2006.01) |
| *G16H 40/67* | (2018.01) |
| *A61N 1/39* | (2006.01) |

(Continued)

(52) U.S. Cl.
CPC ............ *A61B 5/046* (2013.01); *A61B 5/0006* (2013.01); *A61B 5/0031* (2013.01); *A61B 5/686* (2013.01); *A61B 5/02405* (2013.01); *A61B 5/04012* (2013.01); *A61N 1/3624* (2013.01); *A61N 1/3925* (2013.01); *G16H 40/67* (2018.01)

(58) Field of Classification Search
CPC ....... A61B 5/046; A61B 5/686; A61B 5/0031; A61B 5/0006; A61B 5/02405; A61B 5/04012; A61N 1/3624; A61N 1/3925; G16H 40/67
See application file for complete search history.

(56) References Cited

U.S. PATENT DOCUMENTS

| | | |
|---|---|---|
| 2004/0092836 A1 | 5/2004 | Ritscher et al. |
| 2006/0247547 A1 | 11/2006 | Sarkar et al. |

(Continued)

FOREIGN PATENT DOCUMENTS

| | | |
|---|---|---|
| CN | 110167439 A | 8/2019 |

OTHER PUBLICATIONS

"International Application Serial No. PCT/US2018/012810, International Preliminary Report on Patentability dated Jul. 18, 2019", 7 pgs.

(Continued)

*Primary Examiner* — Mallika D Fairchild
(74) *Attorney, Agent, or Firm* — Schwegman Lundberg & Woessner, P.A.

(57) ABSTRACT

This document discusses, among other things, apparatus, systems, and methods to determine a first atrial fibrillation (AF) indication using received information about a heart over a first period, to cluster depolarization information about the heart over the first period, and to discriminate between an atrial fibrillation (AF) event and a non-AF event in the first period using the determined first AF indication the clustered depolarization information.

20 Claims, 12 Drawing Sheets

(51) Int. Cl.
   *A61B 5/024*      (2006.01)
   *A61N 1/362*      (2006.01)

(56) References Cited

U.S. PATENT DOCUMENTS

2016/0213270 A1    7/2016  Cao et al.
2016/0287115 A1*  10/2016  Perschbacher ....... A61B 5/0031

OTHER PUBLICATIONS

"International Application Serial No. PCT/US2018/012810, International Search Report dated May 3, 2018", 4 pgs.
"International Application Serial No. PCT/US2018/012810, Written Opinion dated May 3, 2018", 5 pgs.

* cited by examiner

ATRIAL FIBRILLATION DISCRIMINATION USING HEART RATE CLUSTERING

CLAIM OF PRIORITY

This application claims the benefit of priority under 35 U.S.C. § 119(e) of U.S. Provisional Patent Application Ser. No. 62/444,046, filed on Jan. 9, 2017, which is herein incorporated by reference in its entirety.

TECHNICAL FIELD

This document relates generally to medical devices, and more particularly, but not by way of limitation, to apparatus, systems, and methods of atrial fibrillation discrimination using heart rate clustering.

BACKGROUND

Ambulatory medical devices include implantable medical devices (IMDs), wearable medical devices, handheld medical devices, and other medical devices. IMDs can include cardiac rhythm management (CRM) devices, such as implantable pacemakers, implantable cardioverter defibrillators (ICDs), subcutaneous implantable cardioverter defibrillators (S-ICDs), cardiac resynchronization therapy devices (CRTs), a combination of such, or one or more other devices used to monitor, detect, or treat various cardiac conditions that can result in a reduced ability of a heart to sufficiently deliver blood to a body. In some cases, heart conditions may lead to rapid, irregular, or inefficient heart contractions, such as atrial fibrillation (AF) or one or more other conditions. To alleviate such conditions, various medical devices can be used to monitor heart activity or to provide electrical stimulation to optimize or control contractions of the heart.

Traditional cardiac rhythm management (CRM) devices, such as pacemakers or defibrillators, include subcutaneous devices implanted in a chest of a patient, having one or more leads to position one or more electrodes or other sensors at various locations in the heart, such as in one or more of the atria or ventricles. In certain examples, the one or more leads can include a pressure sensor positioned in the heart and coupled to the CRM device through a conductor in the lead. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

In certain examples, IMDs can include diagnostic-only devices, such as implantable loop recorders (ILRs) or subcutaneously implantable heart failure monitors (SubQ HFMs), including one or more sense amplifiers to monitor electrical heart activity within a patient, or one or more sensors to monitor one or more other internal patient parameters. Subcutaneous implantable devices can include electrodes that are able to sense cardiac signals without being in direct contact with the heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Wearable medical devices can include wearable cardioverter defibrillators (WCDs) or wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Handheld medical devices can include personal data assistants (PDAs) and smartphones. The handheld devices can be diagnostic devices that record an electrocardiograph (ECG) or other physiological parameter while the device is resting in a patient hand or being held to a patient chest.

CRM devices can be implantable, but in some situations may not include dedicated atrial sensing capability. Additionally, some diagnostic-only implantable, wearable, and handheld devices do not include dedicated atrial sensing capability. Patients with these types of devices may develop atrial arrhythmias, such as atrial fibrillation (AF). Knowledge that a specific patient is experiencing AF can be useful to physicians and clinicians for diagnostic purposes or to tailor performance of a medical device to that patient's needs to provide the most effective patient therapy.

SUMMARY

This document discusses, among other things, apparatus, systems, and methods to discriminate an atrial fibrillation (AF) event from non-AF event using, among other things, clustered depolarization information. The apparatus, systems, or methods disclosed herein can, among other things, determine a first AF indication using received information about a heart over a first period, cluster depolarization information about the heart over the first period, and discriminate between an AF event and a non-AF event in the first period using the determined first AF indication the clustered depolarization information. The depolarization information can include, among other things, ventricular depolarization information, heart rate (HR) information, or one or more other types of depolarization information.

An example (e.g., "Example 1") of subject matter (e.g., a system) may include an atrial fibrillation (AF) detection circuit configured to receive information about a heart over a first period including a number of cardiac intervals, and to discriminate between an AF event and a non-AF event, the AF detection circuit including: a first AF detection circuit configured to determine a first AF indication in the first period using the received information about the heart; and a second AF detection circuit configured to receive depolarization information about the heart over the first period, and to cluster the received depolarization information, wherein the AF detection circuit is configured to discriminate between an AF event and a non-AF event in the first period using the determined first AF indication and the clustered depolarization information.

In Example 2, the subject matter of Example 1 may optionally be configured such that, if the first AF indication is indicative of an AF event in the first period, the second AF detection circuit is configured to cluster the received depolarization information to verify the first AF indication, and the AF detection circuit is configured to provide an indication of an AF event in the first period if the first AF indication is indicative of an AF event in the first period and the clustered depolarization information is indicative of an AF event in the first period.

In Example 3, the subject matter any one or more of Examples 1-2 may optionally be configured such that, if the first AF indication is indicative of a non-AF event over the first period, the second AF detection circuit does not cluster the received depolarization information, and the AF detection circuit is configured to provide an indication of a non-AF event over the first period using only the first AF indication.

In Example 4, the subject matter any one or more of Examples 1-3 may optionally be configured such that the AF detection circuit is configured to receive information about a ventricle of the heart, wherein the depolarization information includes ventricular depolarization information, and the first AF detection circuit is configured to determine a ventricular rate stability over the first period using the ventricular depolarization information, and to determine the first AF indication using the determined ventricular rate stability.

In Example 5, the subject matter any one or more of Examples 1-4 may optionally be configured such that the AF detection circuit is configured to receive information about a ventricle of the heart, including ventricular depolarizations, over the first period, and the first AF detection circuit is configured to determine the first AF indication using V-V intervals between successive ventricular depolarizations over the first period.

In Example 6, the subject matter any one or more of Examples 1-5 may optionally be configured such that the received depolarization information includes ventricular depolarization information for cardiac intervals in the first period, the AF detection circuit is configured to bin the cardiac intervals into separate rate bins using the received ventricular depolarization information, the second AF detection circuit is to determine a number of clusters over the first period, and a cluster includes a group of successive rate bins having bin counts greater than a bin threshold and a group bin count greater than a threshold percentage of the number cardiac intervals over the first period.

In Example 7, the subject matter any one or more of Examples 1-6 may optionally be configured such that the AF detection circuit is configured to provide an indication of an AF event in the first period if the first AF indication is indicative of an AF event in the first period and the determined number of clusters over the first period is less than or equal to a cluster threshold.

In Example 8, the subject matter any one or more of Examples 1-7 may optionally be configured such that the number of cardiac intervals includes a positive integer, X, greater than or equal to 100, the separate rate bins have respective values at least X/20 beats apart, the bin threshold is at least 4% of X, the threshold percentage is at least 20% of X, and the cluster threshold is less than or equal to 1.

An example (e.g., "Example 9") of subject matter (e.g., a method) may include receiving information about a heart over a first period including a number of cardiac intervals using an atrial fibrillation (AF) detection circuit; determining, using a first AF detection circuit, a first AF indication in the first period using the received information about the heart; and if the first AF indication is indicative of an AF event in the first period: receiving depolarization information about the heart over the first period using a second AF detection circuit; clustering, using the second AF detection circuit, the received depolarization information; and discriminating between an AF event and a non-AF event in the first period using the clustered depolarization information.

In Example 10, the subject matter of any one or more of Examples 1-9 may optionally be configured to include providing an indication of an AF event in the first period using the AF detection circuit if the first AF indication is indicative of an AF event in the first period and the clustered depolarization information is indicative of an AF event in the first period.

In Example 11, the subject matter any one or more of Examples 1-10 may optionally be configured to include, if the first AF indication is indicative of a non-AF event over the first period, providing an indication of a non-AF event over the first period using the AF detection circuit.

In Example 12, the subject matter any one or more of Examples 1-11 may optionally be configured such that receiving information about the heart over the first period includes receiving information about a ventricle of the heart over the first period, receiving depolarization information about the heart over the first period includes receiving a ventricular rate, and the method further optionally including: determining a ventricular rate stability over the first period using the second AF detection circuit, wherein determining the first AF indication in the first period using the received information about the heart includes using the determined ventricular rate stability.

In Example 13, the subject matter any one or more of Examples 1-12 may optionally be configured such that receiving information about the heart over the first period includes receiving information about a ventricle of the heart, including ventricular depolarizations, over the first period, and determining the first AF indication in the first period includes using V-V intervals between successive ventricular depolarizations over the first period.

In Example 14, the subject matter any one or more of Examples 1-13 may optionally be configured such that receiving depolarization information about the heart over the first period includes receiving ventricular depolarization information for cardiac intervals in the first period, and clustering the received depolarization information includes: binning the cardiac intervals into separate rate bins using the received ventricular depolarization information; and determining a number of clusters over the first period, wherein a cluster includes a group of successive rate bins having bin counts greater than a bin threshold and a group bin count greater than a threshold percentage of the number of cardiac intervals over the first period.

In Example 15, the subject matter any one or more of Examples 1-14 may optionally be configured to include providing an indication of an AF event in the first period if the first AF indication is indicative of an AF event in the first period and the determined number of clusters over the first period is less than or equal to a cluster threshold.

In Example 16, the subject matter any one or more of Examples 1-15 may optionally be configured such that the number of cardiac intervals includes a positive integer, X, greater than or equal to 100, the separate rate bins have respective values at least X/20 beats apart, the bin threshold is at least 4% of X, the threshold percentage is at least 20% of X, and the cluster threshold is less than or equal to 1.

An example (e.g., "Example 17") of subject matter (e.g., at least one machine-readable medium including instructions that, when performed by a medical device, cause the medical device to perform instructions) may include instructions that, when performed by a medical device, cause the medical device to: receive information about a heart over a first period including a number of cardiac intervals; determine a first atrial fibrillation (AF) indication in the first period using the received information about the heart; and if the first AF indication is indicative of an AF event in the first period: receive depolarization information about the heart over the first period; cluster the received depolarization information; and discriminate between an AF event and a non-AF event in the first period using the clustered depolarization information.

In Example 18, the subject matter of any one or more of Example 1-17 may optionally be configured to include instructions that, when performed by the medical device, cause the medical device to: provide an indication of an AF event in the first period if the first AF indication is indicative of an AF event in the first period and the clustered depolarization information is indicative of an AF event in the first period.

In Example 19, the subject matter of any one or more of Examples 1-18 may optionally be configured to include instructions that, when performed by the medical device, cause the medical device to receive depolarization information about the heart over the first period include instructions to: receive ventricular depolarization information for cardiac intervals in the first period, wherein the instructions that, when performed by the medical device, cause the medical device to cluster the received depolarization information include instructions to: bin the cardiac intervals into separate rate bins using the received ventricular depolarization information; and determine a number of clusters over the first period, wherein a cluster includes a group of successive rate bins having bin counts greater than a bin threshold and a group bin count greater than a threshold percentage of the number of cardiac intervals over the first period.

In Example 20, the subject matter of any one or more of Examples 1-19 may optionally be configured to include instructions that, when performed by the medical device, cause the medical device to: provide an indication of an AF event in the first period if the first AF indication is indicative of an AF event in the first period and the determined number of clusters over the first period is less than or equal to a cluster threshold, wherein the number of cardiac intervals includes a positive integer, X, greater than or equal to 100, the separate rate bins have respective values at least X/20 beats apart, and the bin threshold is at least 4% of X, the threshold percentage is at least 20% of X, and the cluster threshold is less than or equal to 1.

An example (e.g., "Example 21") of subject matter (e.g., a system or apparatus) may optionally combine any portion or combination of any portion of any one or more of Examples 1-20 to include "means for" performing any portion of any one or more of the functions or methods of Examples 1-20, or a "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Atrial fibrillation (AF) can be detected in a number of ways, such as, for example, morphology analysis of an electrocardiogram (ECG) signal of a heart (e.g., a 12-lead ECG signal), determining one or more density or stability characteristics of a group of cardiac depolarizations (e.g., using a Lorenz plot of sequential depolarization timings), or one or more other ways. Traditional AF detection, for example, using an apparatus or system with or without a separate atrial lead or specific detection of atrial depolarizations, have certain sensitivities and specificities. In general, a higher sensitivity results in a lower specificity, and vice versa, such that to achieve AF detection with high sensitivity, false alarms can be an issue. Existing apparatus or systems may flag candidate AF events for later manual ECG inspection, which can represent a high clinical burden.

The present inventors have recognized, among other things, apparatus, systems, and methods to discriminate between an atrial fibrillation (AF) event and a non-AF event using clustered depolarization information. In an example, such discrimination of AF and non-AF events disclosed herein can supplement traditional, existing AF detection systems and methods, in certain examples, increasing the specificity of existing AF event detection (e.g., reducing false positives), such that system performance can be improved with little to no additional cost. In certain examples, increased specificity of AF detection can reduce the cost of manual ECG inspection. In other examples, existing system performance can be maintained (e.g., high AF detection sensitivity and specificity, etc.) using lower cost or less obtrusive systems, apparatus, and methods. Further, increased specificity of AF detection can lead to storage of a smaller number of potential AF events. As fewer alarms are provided, battery life is extended, fewer unnecessary drugs or procedures will be scheduled, prescribed, or provided, and an overall system savings will be realized.

Figure 1:
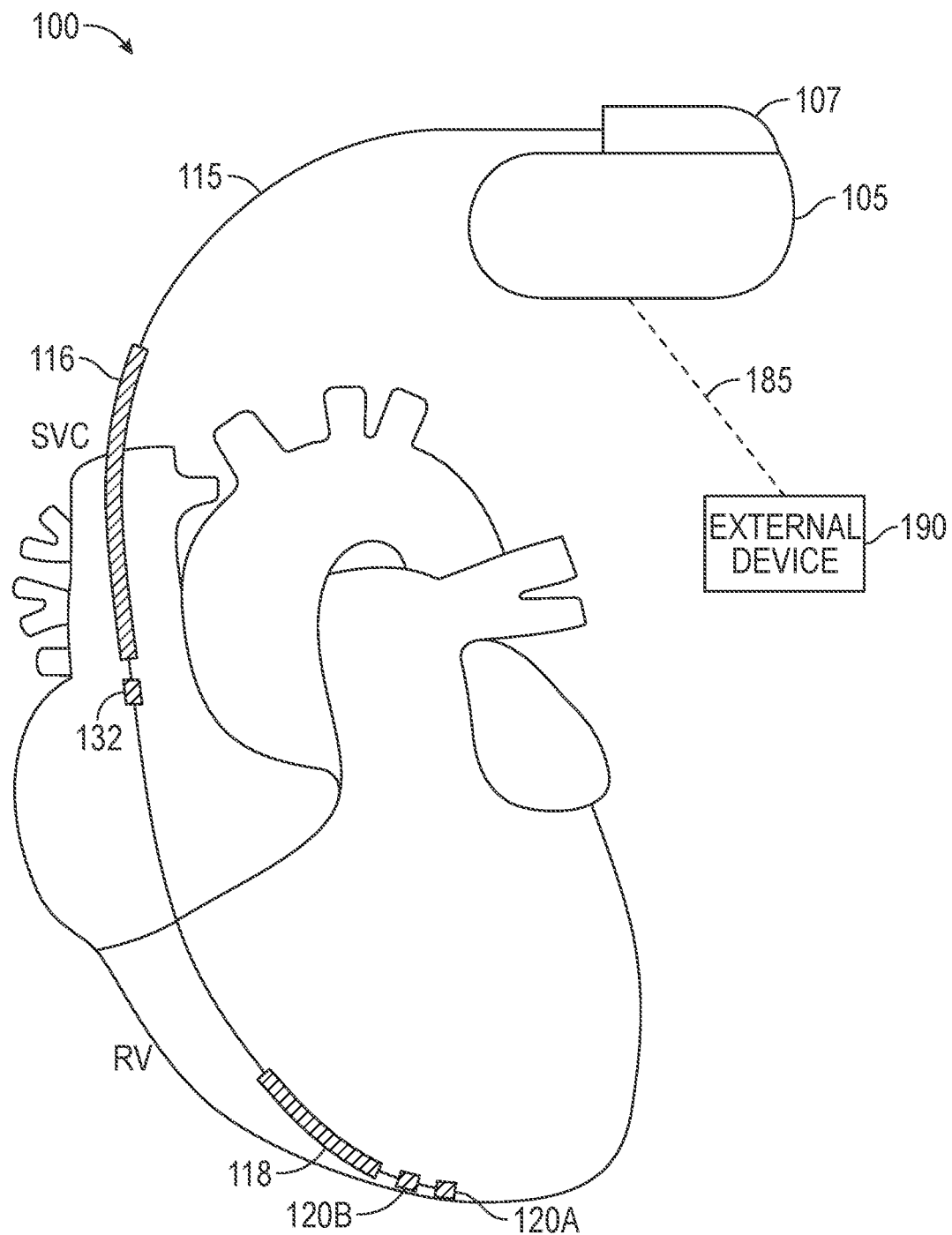
FIG. 1 illustrates an example system including an IMD.

FIG. 1 illustrates an example system 100 including an IMD 105, such as a pacemaker, cardioverter, defibrillator, or one or more other implantable cardiac monitoring or therapy delivery devices configured to detect or treat a cardiac arrhythmia. The IMD 105 can include an electronics unit coupled by one or more cardiac leads 115 to a heart of a patient or subject. The electronics unit of the IMD 105 can include components enclosed in a hermetically-sealed housing (e.g., a canister or "can"). The system 100 can include an IMD programmer or other external system 190 to communicate one or more wireless signals 185 with the IMD 105, such as by using radio frequency (RF) or by one or more other telemetry methods.

The IMD 105 can include a single-chamber device, including a right ventricular (RV) lead 115 having a proximal end and a distal end. The proximal end is coupled to a header 107. The distal end is configured for placement in a RV of a heart. The RV lead 115 can include one or more of a proximal defibrillation electrode 116, a distal defibrillation electrode 118 (e.g., RV Coil), an RV tip electrode 120A, or an RV ring electrode 120B. The defibrillation electrode 116 can be incorporated into the lead body, such as in a location suitable for supraventricular placement in the superior vena cava (e.g., SVC Coil). The RV lead 115 can include a ring electrode 132 (e.g., SVC ring) in the vicinity of the proximal defibrillation electrode 116. The distal defibrillation electrode 118 can be incorporated into the lead body near the distal end, such as for placement in the RV. The RV electrodes 120A, 120B can form a bipolar electrode pair incorporated into the lead body at the lead distal end. The electrodes 116, 118, 120A, 120B can each be electrically coupled to the IMD 105, such as through one or more conductors extending within the lead body. The proximal defibrillation electrode 116, the distal defibrillation electrode 118, or an electrode formed on the housing of the IMD 105 can allow for delivery of cardioversion or defibrillation pulses to the heart. The RV tip electrode 120A, the RV ring electrode 120B, or an electrode formed on the housing of the IMD 105 can allow for sensing an RV electrogram signal representative of RV depolarizations and delivering RV pacing pulses. The IMD 105 can includes a sense amplifier circuit to provide amplification or filtering of the sensed signal. Sensing and pacing can allow the IMD 105 to detect and adjust timing of the heart chamber contractions.

In certain examples, IMDs may not include any electrodes for sensing electrical activity in an atrium. For example, the IMD 105 can be an ICD with single ventricular chamber sensing. The ICD can include an electrode attached to a single ventricular lead, and use intrinsic cardiac signals sensed with the ventricular electrode for arrhythmia detection or discrimination (e.g., by rate sensing and/or depolarization signal morphology analysis).

In other examples, IMDs can include diagnostic-only devices that do not provide electrical therapy to the patient. Such a device can include a combination of the RV tip electrode 120A, the RV ring electrode 120B, or the electrode formed on the housing of the IMD 105 to allow for sensing of ventricular depolarizations.

Figure 2:
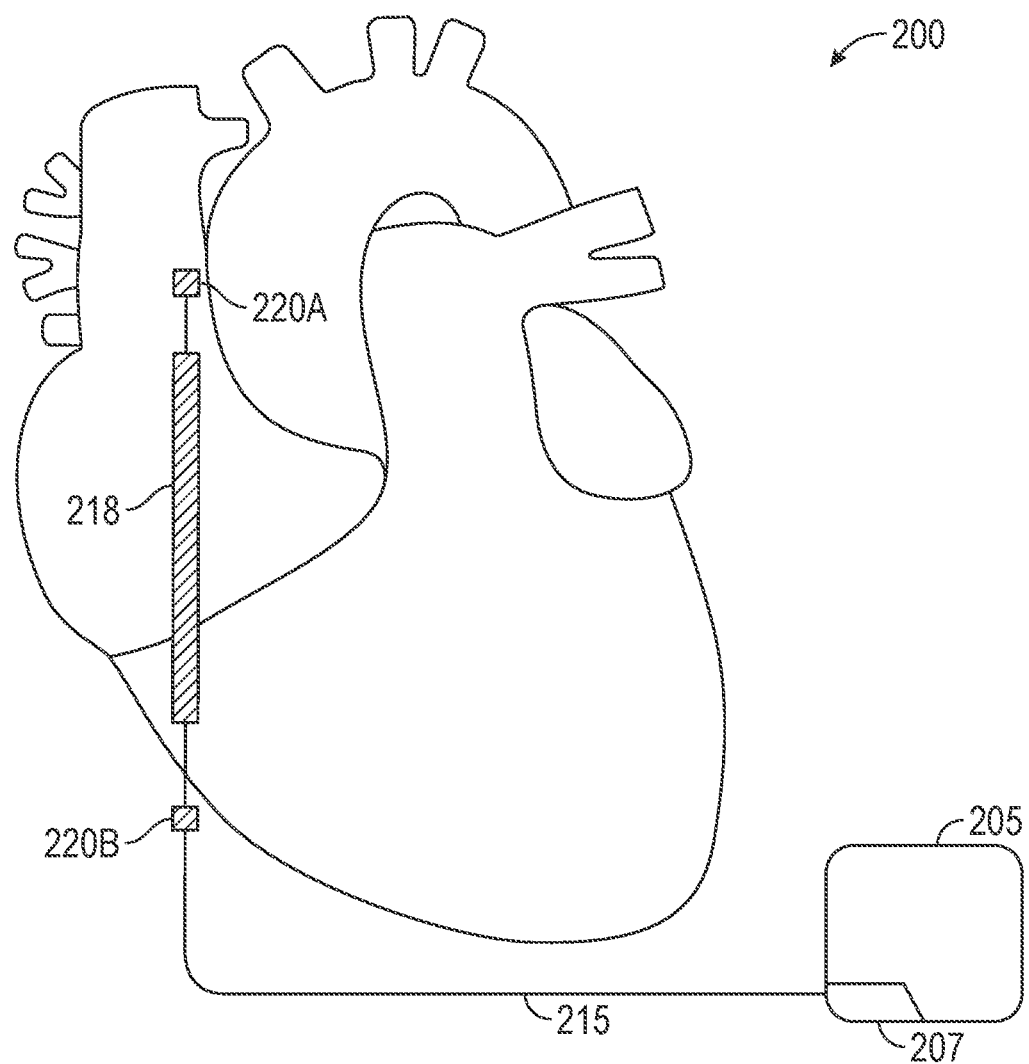
FIG. 2 illustrates an example system including an S-ICD.

FIG. 2 illustrates an example system 200 including an S-ICD 205 and a lead 215. The S-ICD 205 and the lead 215 can be implantable subcutaneously. A proximal end of the lead 215 can be coupled to a header 207. The lead 215 can include a first electrode 220A and a second electrode 220B, such as to sense ventricular depolarizations (e.g., using far-field sensing).

In the example of FIG. 2, the lead 215 does not include any electrodes that directly contact the heart. The lead 215 includes a defibrillation electrode 218, such as a coil electrode. The S-ICD 205 can provide one or more of cardioversion therapy or defibrillation high energy shock therapy to the heart using the defibrillation electrode 218 and an electrode formed on the housing of the S-ICD 205. In some examples, the S-ICD 205 can provide pacing pulses for anti-tachycardia therapy or bradycardia therapy. Direct atrial sensing is not provided in the arrangement of the electrodes.

Figure 3:
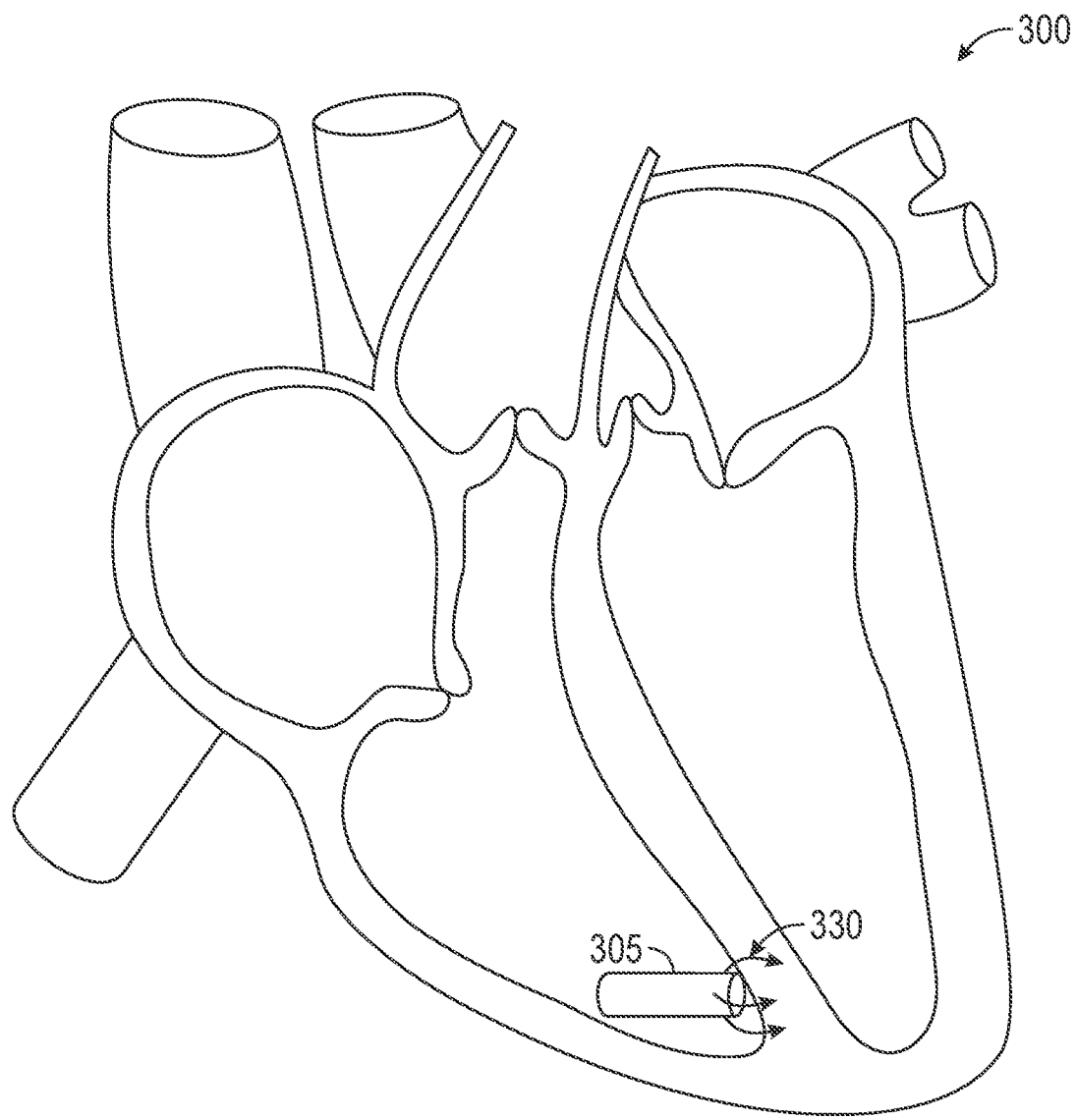
FIG. 3 illustrates an example system including a leadless pacemaker.

FIG. 3 illustrates an example system 300 including a leadless pacemaker 305 positioned at an endocardium within a ventricular chamber. In other examples, the leadless pacemaker 305 can be positioned at one or more other locations of the heart, or can include one or more other leadless devices positioned in or on the heart.

In certain examples, the leadless pacemaker 305 can have a cylindrical or bullet shaped housing, and can include one or more electrodes arranged along the cylindrical housing to sense electrical signals of the heart or to provide electrical stimulation for pacing the heart. In certain examples, the one or more electrodes can be used for communication, or the leadless pacemaker 305 can include one or more other communication or telemetry circuits or components.

The leadless pacemaker 305 can include a mechanism 330 to fix the pacemaker to the myocardium. Examples of the fixation mechanism can include one or more tines, one or more barbed tines, or one or more helix or other-shaped fixation mechanisms.

Other examples of an IMD include an implantable loop recorder (ILR), a diagnostic device without leads in the heart, and a neurostimulator (including but not limited to vagus nerve stimulators, baroreceptor stimulators, or spinal cord stimulators), or other IMD including, or not including, an electrode positioned in an atrium.

Figure 4:
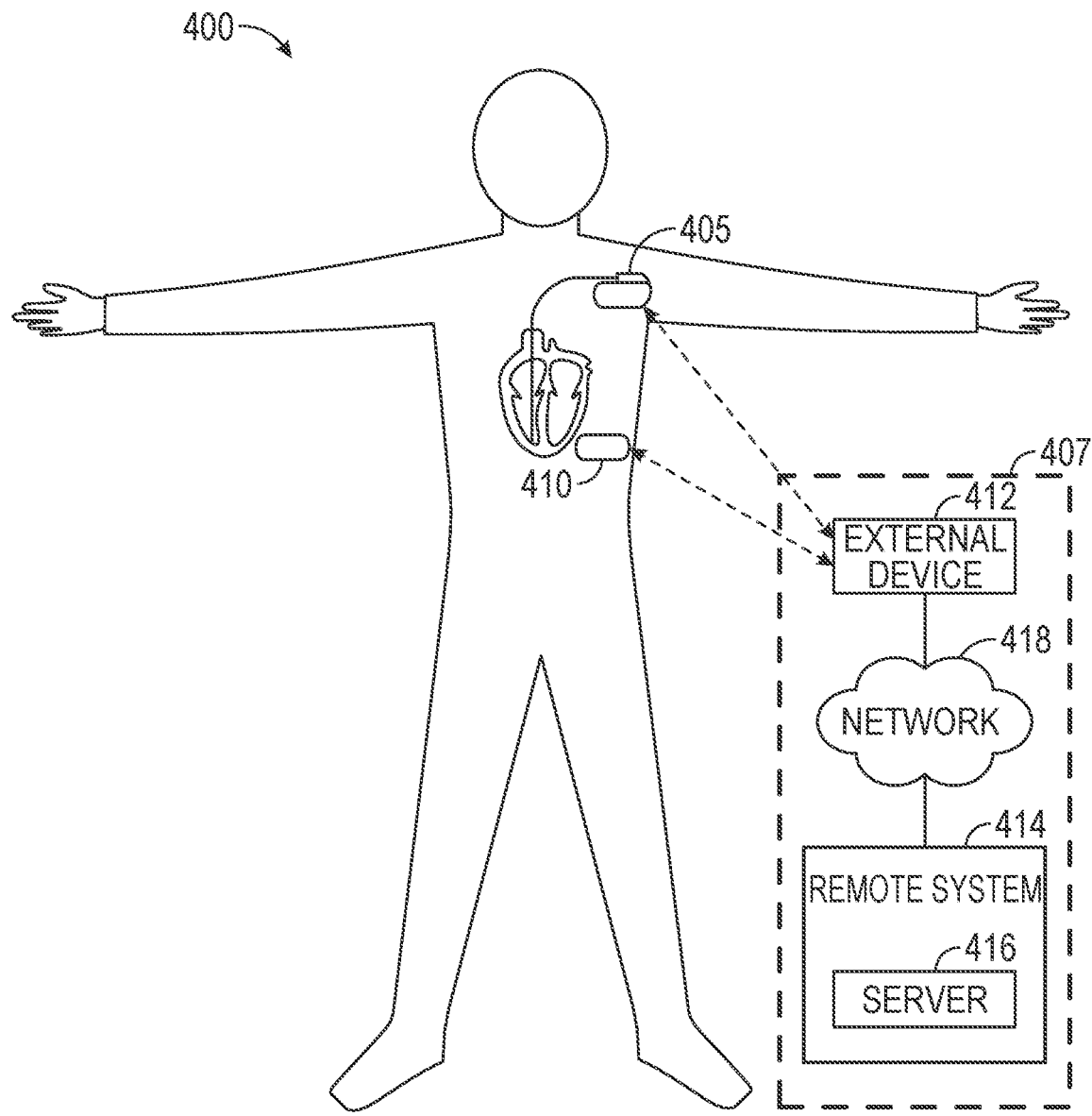
FIG. 4 illustrates an example system including one or more ambulatory medical devices and a communication system.

FIG. 4 illustrates an example system 400 including one or more ambulatory medical devices, such as a conventionally or subcutaneously implantable medical device 405 or a wearable medical device 410, and a communication system 407. In an example, the one or more ambulatory medical devices can include a communication circuit (e.g., a telemetry circuit) to communicate information from a heart, such as heart rate (HR) information or an indication of atrial fibrillation (AF) to the communication system 407.

The communication system 407 can include an external communication device 412, a remote system 414, and a network 418 (e.g., the internet, a proprietary computer network, a cellular phone network, etc.). The remote system 414 can include a server 416 remotely located from the external communication device 412 and the subject to perform patient management functions. In certain examples, the external communication device 412 can include a medical device programmer to program therapy parameters of a device-based therapy provided by the implantable medical device 405. In an example, one or both of the external communication device 412 and the remote system 414 can include a display to present the indication of AF to a user, such as a clinician.

Figure 5:
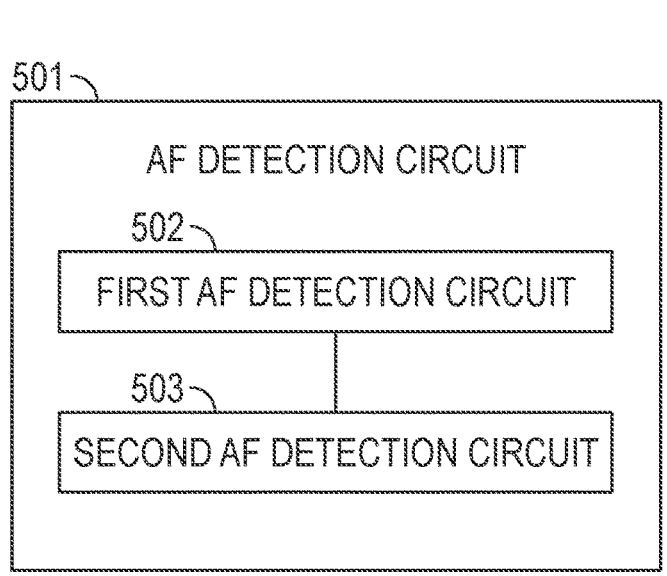
FIG. 5 illustrates an example system including first and second atrial fibrillation (AF) detection circuits.

FIG. 5 illustrates an example system 500 including an atrial fibrillation (AF) detection circuit 501 configured to receive information about a heart of a patient over a first period including a number of cardiac intervals, and to discriminate between an AF event and a non-AF event. In an example, the information about a heart can include electrical or mechanical information about the heart detected, for example, using one or more of the apparatus, systems, or methods described herein.

The information about the heart can include electrical cardiac information, such as depolarization information, including ventricular depolarization, heart rate (HR), timing between one or more cardiac events in the same or different cardiac intervals (e.g., RR or VV intervals, etc.), etc. In an example, the cardiac interval can include one heart beat of the heart of the patient, such as between sequential R waves, P waves, the beginning of the QRS complex, or one or more other detectable cardiac events, etc. In other examples, the information about the heart can include mechanical cardiac information, such as cardiac wall motion, heart sounds, etc.

The number of cardiac intervals can include a number between several beats and days of cardiac intervals. In an example, the number of cardiac intervals can include a number that provides valuable data analysis, yet current enough to be considered active monitoring, such as one or several minutes of cardiac intervals (e.g., 1 minute, 3 minutes, etc.), representing, in various examples, 50 cardiac intervals (beats), 100 cardiac intervals, 300 cardiac intervals, etc. In other examples, other periods including more or less cardiac intervals can be used.

In an example, the AF detection apparatus, systems, or methods described herein can supplement or improve traditional, existing AF detection systems, clustering received depolarization information and using such clustered information to discriminate between an AF event and a non-AF event, with a greater specificity than the traditional, existing AF detection alone.

The AF detection circuit 501 can include a first AF detection circuit 502 configured to determine a first AF indication (e.g., using one or more traditional, existing AF detection apparatus, systems, or methods) in the first period using the received information about the heart.

The AF detection circuit 501 can include a second AF detection circuit 503 configured to receive depolarization information about the heart over the first period, and to cluster the received depolarization information. In an example, the received information about the heart, such as used to determine the first AF indication, can include the received depolarization information. In other examples, the received information about the heart can include other electrical or mechanical information about the heart.

The AF detection circuit 501 can be configured to discriminate between an AF event and a non-AF event in the first period using the determined first AF indication and the clustered depolarization information. In an example, if the first AF indication is indicative of an AF event in the first period, the second AF detection circuit 503 can be configured to cluster the received depolarization information, for example, to verify the first AF indication as an AF event or a non-AF event. The AF detection circuit 501 can be configured to provide an indication of an AF event in the first period if the first AF indication is indicative of an AF event in the first period and the clustered depolarization information is indicative of an AF event in the first period. In certain examples, the indication can include a notification, such as to a user, clinician, or other device or process, etc.

In an example, if the first AF indication is indicative of a non-AF event over the first period, the second AF detection circuit 503 may not receive the depolarization information, or separately, may not cluster received depolarization information. In such example, the AF detection circuit 501 can be configured to provide an indication of a non-AF event over the first period using only the first AF indication.

In an example, the first AF detection circuit 502 and the second AF detection circuit 503 can be separate circuits, sub-circuits of the AF detection circuit 501, or can include a single circuit, such as the AF detection circuit 501, configured to perform the functions of each, as described herein. For example, the second AF detection circuit 503 or the functions of such described herein can modify an existing AF detection circuit or algorithm, and accordingly, can be added to an existing system without greatly modifying the first AF detection circuit 502. In other examples, the AF detection circuit 501 can include a single circuit configured to perform the functions of the first and second AF detection circuits 502, 503 as described herein.

Figure 6:
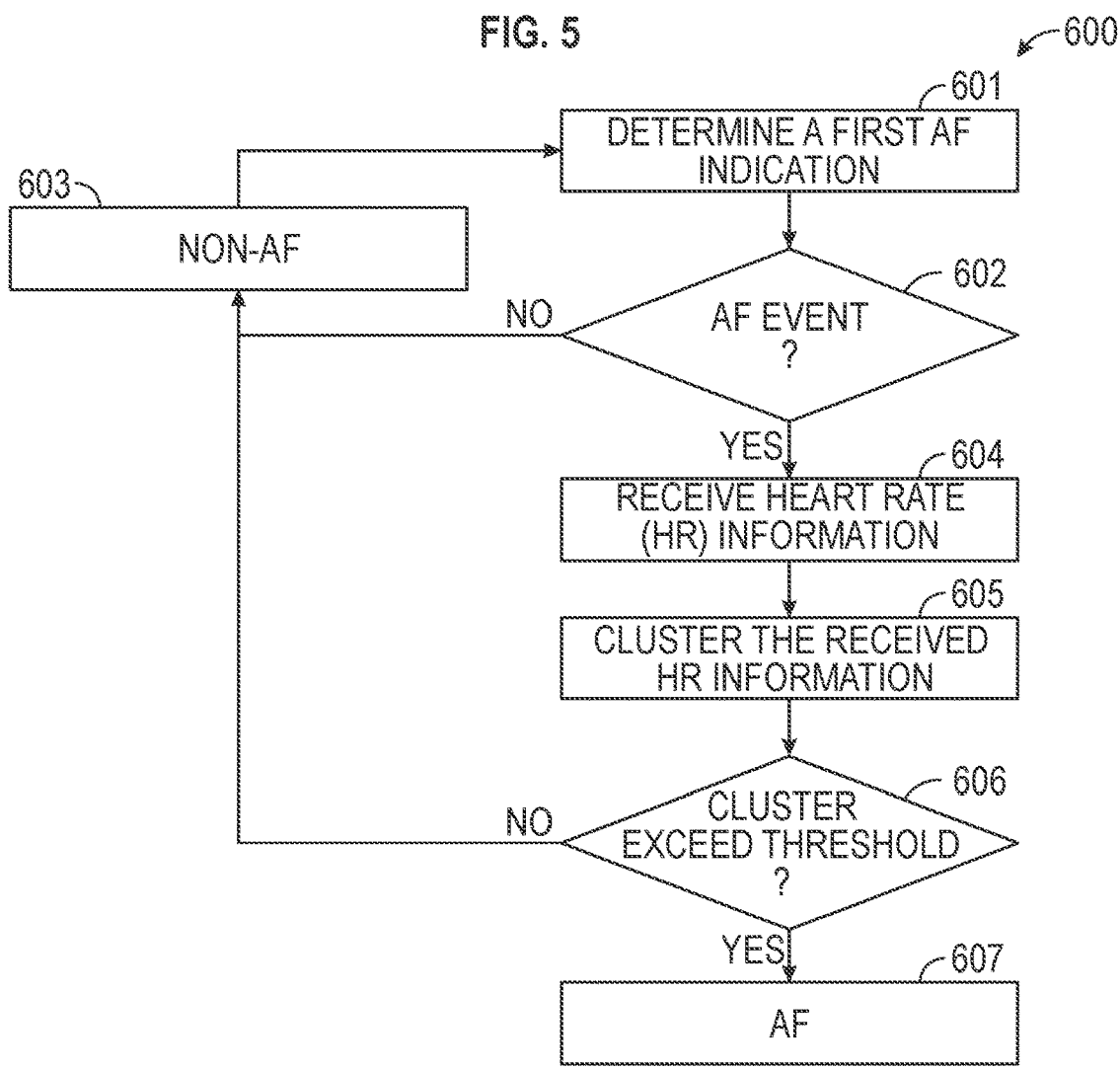
FIG. 6 illustrates an example method to discriminate between atrial fibrillation (AF) and non-AF using a first AF indication and clustered heart rate (HR) information.

FIG. 6 illustrates generally an example method 600 to discriminate between atrial fibrillation (AF) and non-AF using a first AF indication and clustered heart rate (HR) information.

In an example, information about a heart can be received over a first period including a number of cardiac intervals, such as using an AF detection circuit. The information about the heart can include electrical or mechanical information about the heart of a patient, including information about a ventricle of the heart.

At 601, a first AF indication in the first period can be determined, for example, using the received information about the heart, such as by using a first AF detection circuit. In an example, determining a first AF indication can include determining a rate stability over the first period, such as using a Lorenz plot, etc. The rate stability can, in certain examples, include a determined ventricular rate stability, detected, for example, using an apparatus or system not having a specific atrial sense lead. The determined first AF indication can indicate that an AF event occurred over the first period, or that at a non-AF event occurred over the first period (e.g., that no AF event occurred over the first period).

At 602, if the first AF indication is indicative of a non-AF event over the first period, or no AF event over the first period, then, at 603, an indication of a non-AF event can be provided, such as to a user, clinician, or other medical device or process, etc. At 602, if the first AF indication is indicative of an AF event over the first period, such that at least one AF event is likely to have occurred over the first period, then process can continue.

At 605, the received HR or other depolarization information can be clustered, such as using a second AF detection circuit. In an example, clustering the depolarization information can include binning depolarization or cardiac intervals (e.g., HR values, RR or VV intervals, or one or more other cardiac or depolarization intervals, etc.), or information derived from such intervals (e.g., differences in intervals or rate, etc.) over the first period, and counting a number of clusters in the first period.

At 606, if the number of clusters determined at 605 does not meet or exceed a threshold, then, at 603, an indication of a non-AF event can be provided, in contrast to the determined indication at 601. In certain examples, the clustered information can overrule the determined first AF indication. At 606, if the number of clusters determined at 605 is less than or equal to the threshold, then, at 607, an indication of an AF event (e.g., at least one AF event, occurring over the first period) can be provided, such as to a user, clinician, or other medical device or process.

Figure 7:
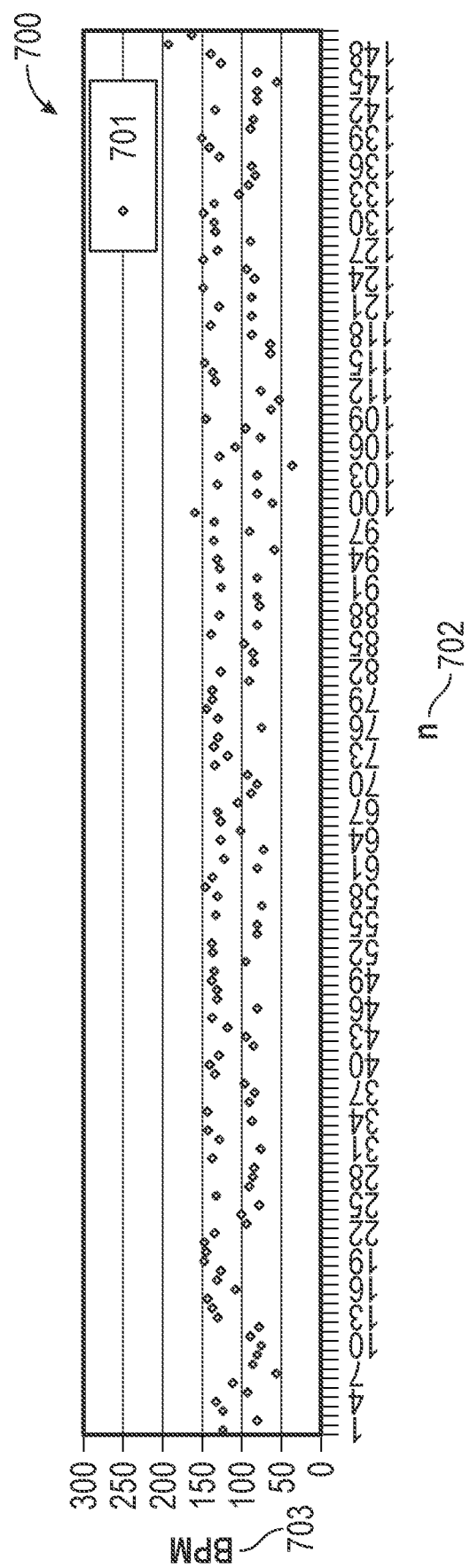
FIG. 7 illustrates an example heart rate (HR) plot illustrating a number of sequential heart beats.

FIG. 7 illustrates an example heart rate (HR) plot 700 illustrating a number (n) 702 of sequential heart beats 701, in beats-per-minute (BPM) 703.

Figure 8:
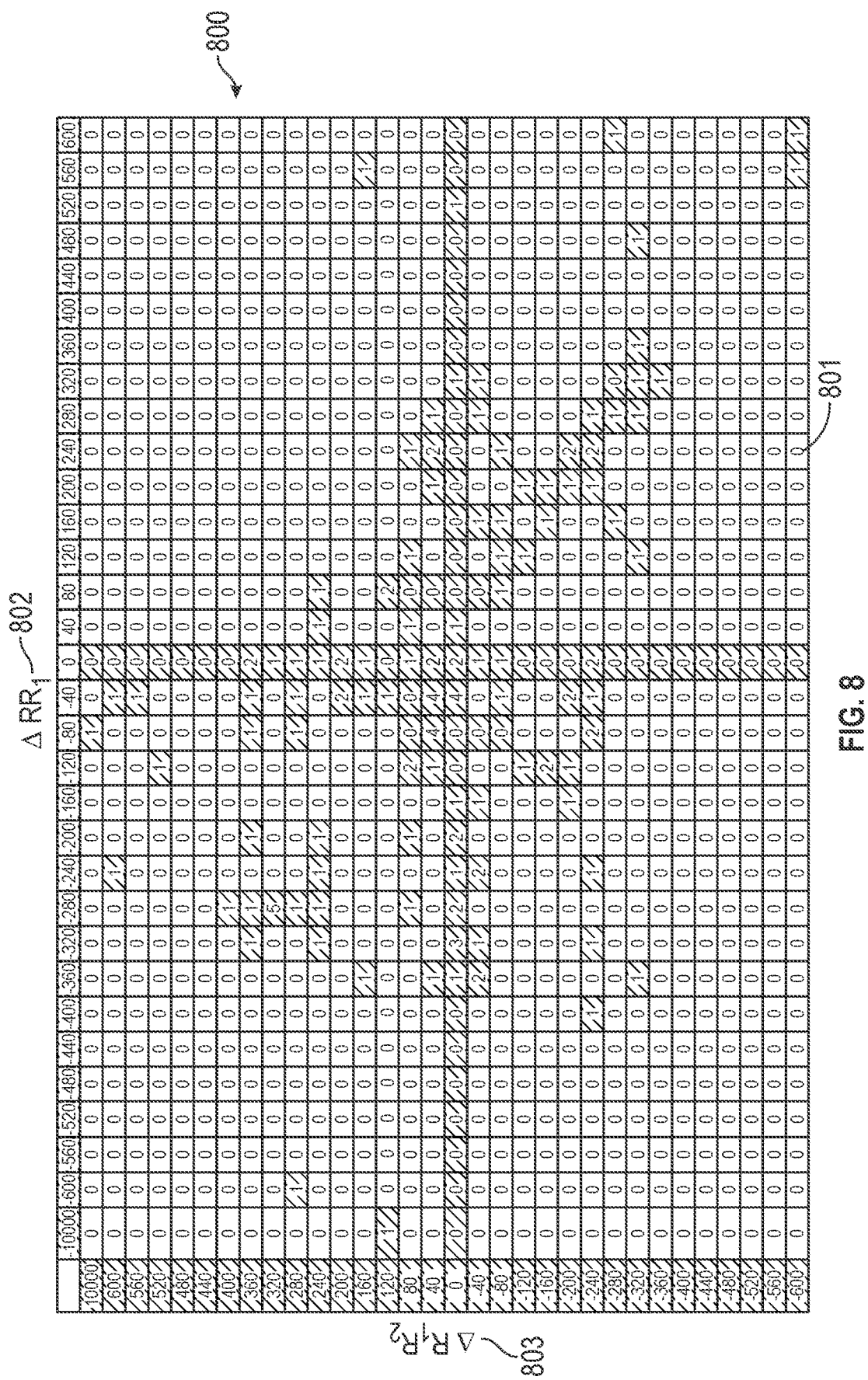
FIG. 8 illustrates an example Lorenz plot of heart beat data.

FIG. 8 illustrates an example Lorenz plot 800 of the heart beat data from FIG. 7, illustrating sequential depolarization intervals. Data points 801 are represented as delta (Δ) $RR_1$ 802, a difference in interval between first and second sequential depolarizations (e.g., ventricular depolarizations, etc.) in milliseconds (ms), and Δ $R_1R_2$ 803, a difference in interval between second and third sequential depolarizations in milliseconds.

Atrial fibrillation can be characterized as being substantially randomly distributed, within some bounds, and exhibiting few to no repeating patterns. Using traditional, existing AF detection, the data shown in FIGS. 7 and 8 can appear to be AF, as the HR plot 700 is fairly unstable over time, and the values in the Lorenz plot 800 are sufficiently scattered about the plot.

In certain examples, using a Lorenz plot, or using a stability value of successive or double-decrement HR or depolarization interval (RR intervals, in certain examples, normalized to account for increasing or decreasing rates, etc.), if a threshold number of data points are located outside of the center of the plot, an indication of an AF event is determined. For example, for the sum of data points illustrated in FIG. 8, if the number of data points outside of a center, stable boundary (e.g., between 80 ms and −80 ms for each axis) exceeds the number of data points inside the center, stable boundary by a factor greater than a stability threshold (e.g., by a factor of 6, 8, or one or more other factors or thresholds, etc.), then an indication of an AF event can be determined.

In the Lorenz plot 800 of FIG. 8, a relatively small number of data points lie inside the center, stable boundary (e.g., roughly 15 out of 150), well under a stability threshold factor of 1 stable beat for every 8 unstable beats, for example. However, as will be illustrated in the example of FIG. 11, clustering the data of FIGS. 7 and 8 illustrate that the data shown herein, although initially indicating as an AF event, is actually a non-AF event.

Figure 9:
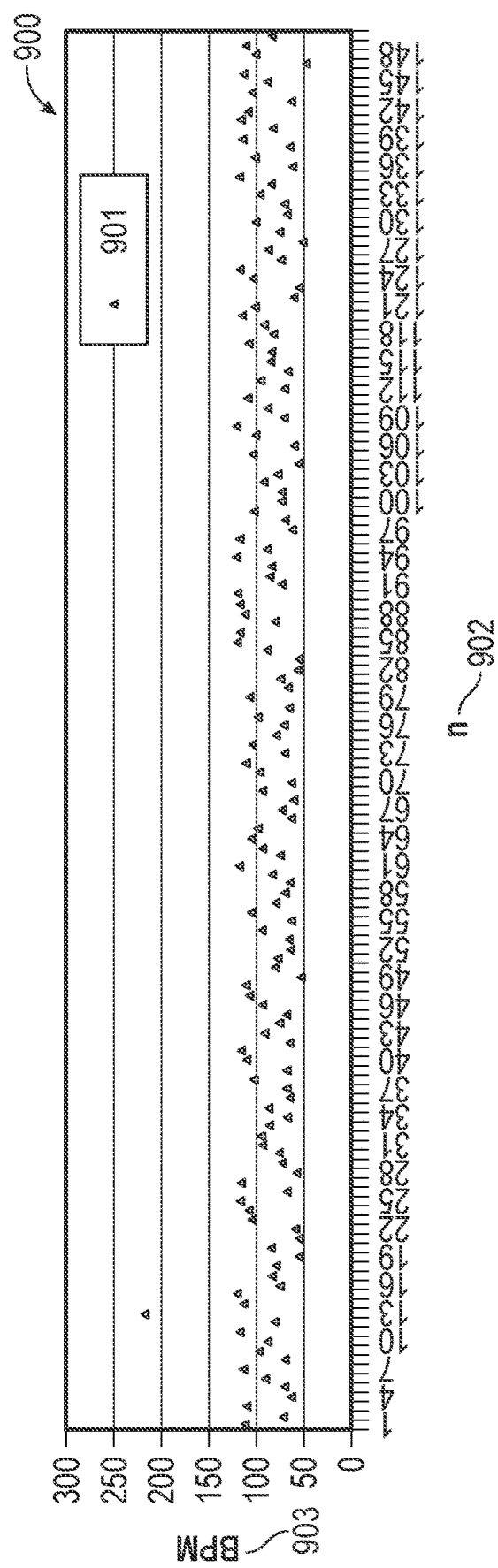
FIG. 9 illustrates an example heart rate (HR) plot illustrating a number (n) of sequential heart beats.

FIG. 9 illustrates an example heart rate (HR) plot 900 illustrating a number (n) 902 of sequential heart beats 901, in beats-per-minute (BPM) 903.

Figure 10:
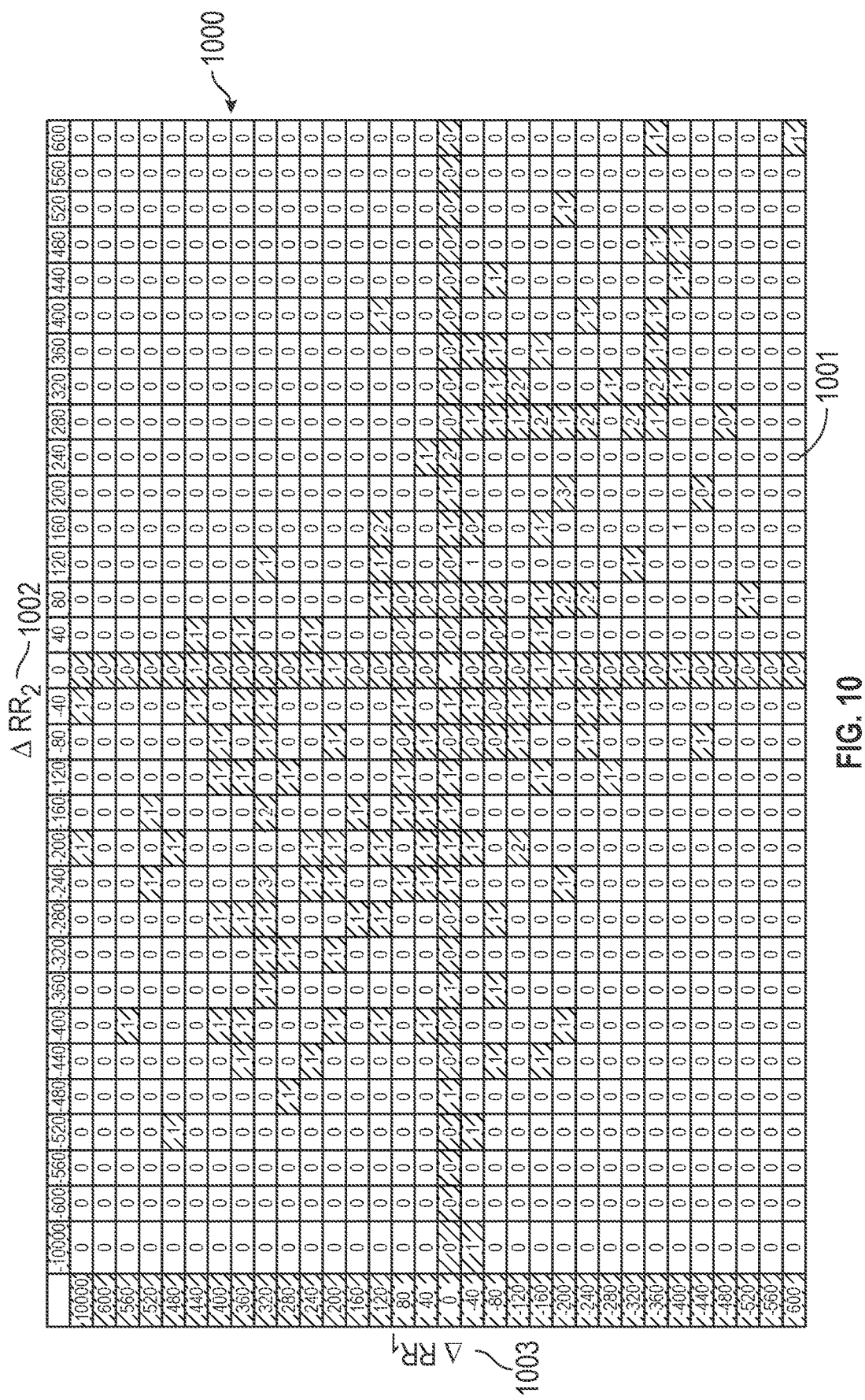
FIG. 10 illustrates an example Lorenz plot of the heart beat data.

FIG. 10 illustrates an example Lorenz plot 1000 of the heart beat data from FIG. 9, illustrating sequential depolarization intervals. Data points 1001 are represented as delta (Δ) $RR_1$ 1002, a difference in interval between first and second sequential depolarizations (e.g., ventricular depolarizations, etc.) in milliseconds (ms), and Δ $R_1R_2$ 1003, a difference in interval between second and third sequential depolarizations in milliseconds.

In the Lorenz plot 1000 of FIG. 10, a substantial number of data points lie outside the center, stable boundary (e.g., between 80 ms and −80 ms for each axis) (e.g., roughly 4 out of 150), well under a stability threshold factor of 1 stable beat for every 8 unstable beats, for example. However, as will be illustrated in the example of FIG. 12, clustering the data of FIGS. 9 and 10 illustrate that the data shown herein is confirmed as an AF event.

Figure 11:
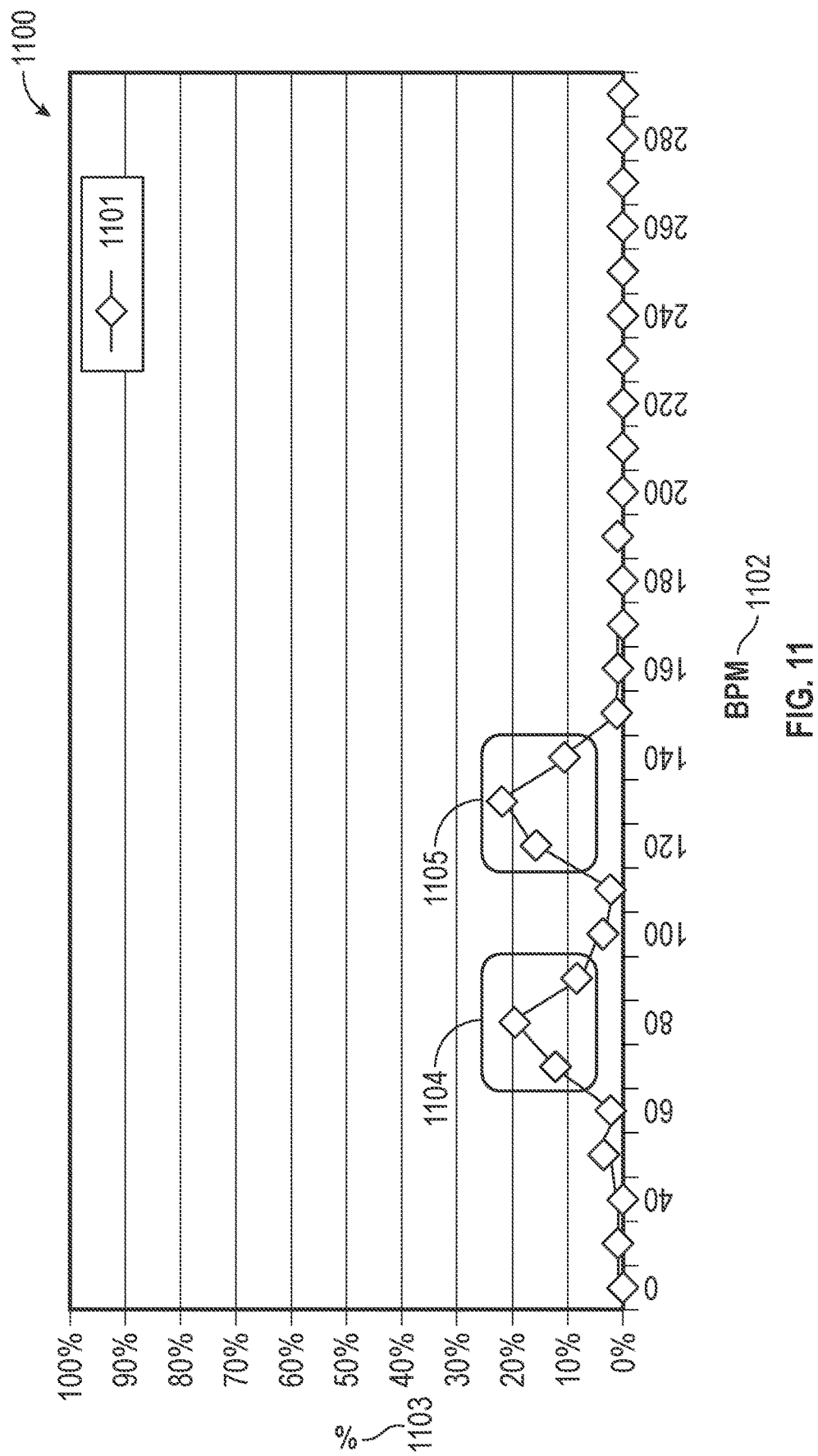
FIG. 11 illustrates generally an example heart rate (HR) histogram illustrating a number of heart beats organized into separate rate bins.

FIG. 11 illustrates generally an example heart rate (HR) histogram 1100 illustrating a number of heart beats 1101 organized into separate rate bins 1102 in beats-per-minute (BPM), by percentage of total heart beats in the HR histogram 1100. In an example, the heart beats 1101 in FIG. 11 can include the heart beats and heart beat data from the examples of FIGS. 7 and 8.

In an example, the number of total heart beats in the histogram can include the number of cardiac intervals over the first period, such as described herein. The separate rate bins 1102 are separated, sequentially, by 10 BPM. In other examples, the separate rate bins 1102 can be separated by more or less BPM, depending on the number of total heart beats in the HR histogram 1100, or the number of cardiac intervals over the first period.

For example, when a HR value of a heart beat 1101 falls within 10 beats of a value of a rate bin, the heart beat 1101 can be assigned to such rate bin. In other examples, the heart beat 1101 can be assigned to a rate bin if the HR of the cardiac interval either above, below, centered, or otherwise situated with respect to the value of the rate bin.

In an example, the HR value of the heart beat 1101 can be erased or not stored after binning the respective heart beat 1101. In other examples, the HR value can be retained, or the heart beat 1101 can be ordered in the respective rate bin according to the HR value, for example.

The HR histogram 1100 includes two clusters, a first cluster 1104 and a second cluster 1105. The first and second clusters 1104, 1105 can be determined using one or more factors, such as a bin threshold and a threshold percentage. In an example, moving across the HR histogram 1100, a cluster can begin (e.g., moving left to right) when the number of heart beats in a rate bin exceeds the bin threshold, such as 4% of the total heart beats in the HR histogram 1100. A cluster includes a group of successive rate bins having bin counts greater than the bin threshold and a group bin count (e.g., an aggregate bin count for the cluster) greater than a threshold percentage of the number of cardiac intervals over the first period, such as 20% of the total heart beats in the HR histogram 1100.

The bin threshold of 4%, the threshold percentage of 20%, and the cluster threshold of less than or equal to 1 have been determined using sample data. Such sample data illustrates that, clustering received depolarization information and discriminating between an AF event and a non-AF event in this matter can reduce falsely identified AF events. For example, across a sample 40,000 periods, a reduction of over 1,000 false positives, non-AF events incorrectly marked as AF events, has been shown, while only falsely removing a single valid AF event. In other examples, other cardiac thresholds, bin thresholds, or threshold percentages can be used, depending on a desired sensitivity or specificity. In certain examples, such thresholds can be set using known or learned cardiac information, or can be dependent on, for example, rate.

Figure 12:
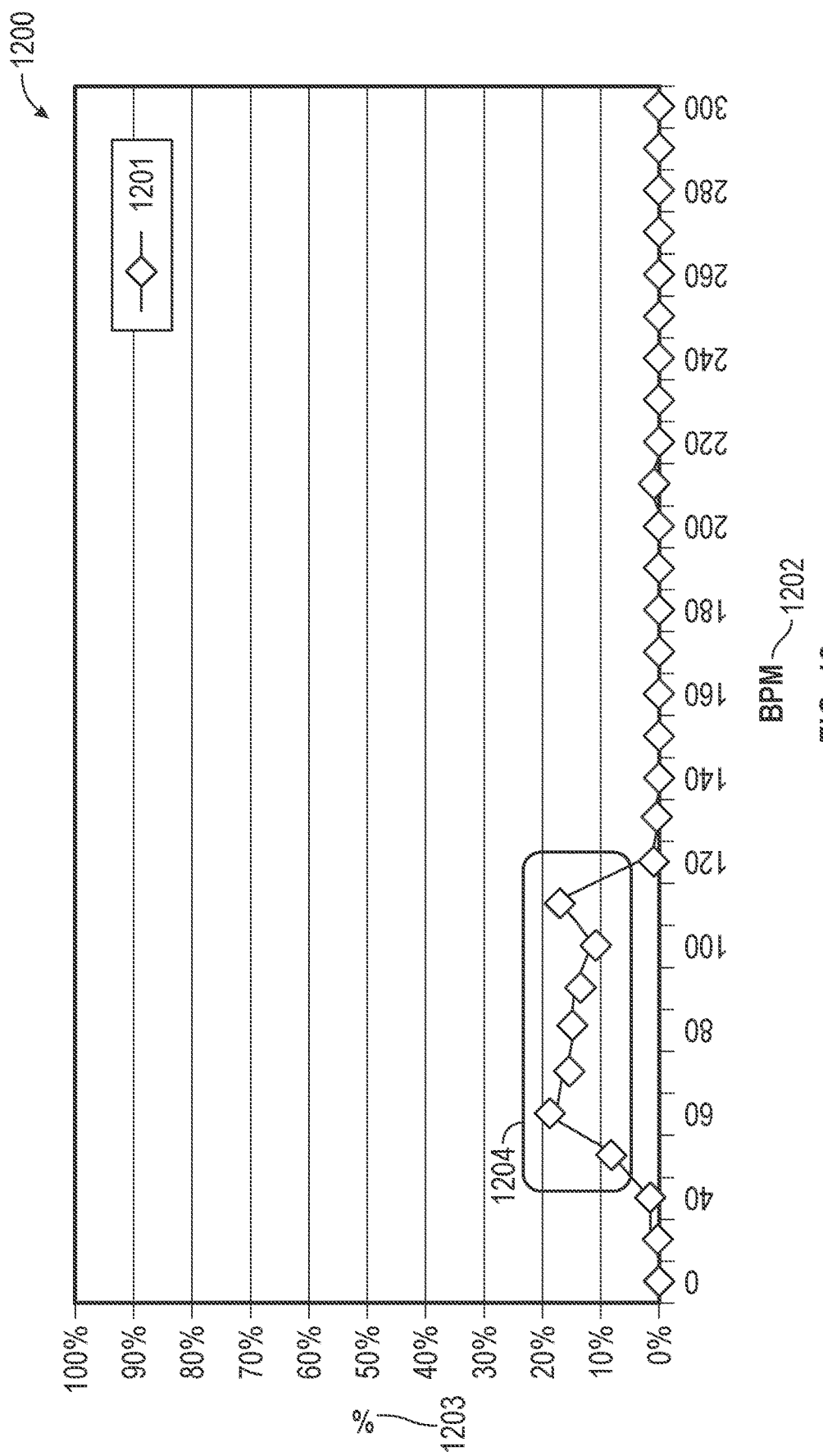
FIG. 12 illustrates generally an example heart rate (HR) histogram illustrating a number of heart beats organized.

Although illustrated using HR in FIG. 11, in certain examples, the clusters can be determined using depolarization information, such as ventricular depolarization information. In an example, the ventricular depolarization information can include HR information. If the determined number of clusters over the first period or number of cardiac intervals exceeds a cluster threshold, an indication indicative of an AF event can be determined FIG. 12 illustrates generally an example heart rate (HR) histogram 1200 illustrating a number of heart beats 1201 organized into separate rate bins 1202 in beats-per-minute (BPM), by percentage of total heart beats in the HR histogram 1200. In an example, the heart beats 1201 in FIG. 12 can include the heart beats and heart beat data from the examples of FIGS. 9 and 10.

In contrast to the example of FIG. 11, which includes two clusters (the first and second clusters 1104, 1105), the HR histogram 1200 of FIG. 12 includes a single cluster 1204, wider than those in FIG. 11. Such a single wide cluster signifies a substantially randomly distributed heart rate across the HR histogram 1200.

As ventricular rate during an AF event is substantially randomly distributed, it can be determined that, even though traditional AF detection would classify the data from FIGS. 8 and 10 as each illustrating AF events, by clustering the depolarization information, the apparatus, systems, and methods described herein can accurately determine that the data of FIGS. 8 and 11 have separate clusters, illustrating a non-random distribution of heart rates, and thus, a non-AF event. In contrast, the apparatus, systems, and methods described herein can accurately confirm that the data of FIGS. 9 and 12 have a single cluster, illustrating a random distribution of heart rates, and thus, an AF event. In other examples, the cluster size can be changed or adjusted (e.g., normalized) based on, for example, heart rate, etc.

In other examples, clustering can be performed on a Lorenz plot, such as that illustrated in FIGS. 7 and 9, instead of a histogram. Further, instead of counting the number of clusters to discriminate an AF event from a non-AF event, one or more peaks can be detected, etc., and we now have a minimum volume of a cluster or one or more other raw or relative values can be used.

Figure 13:
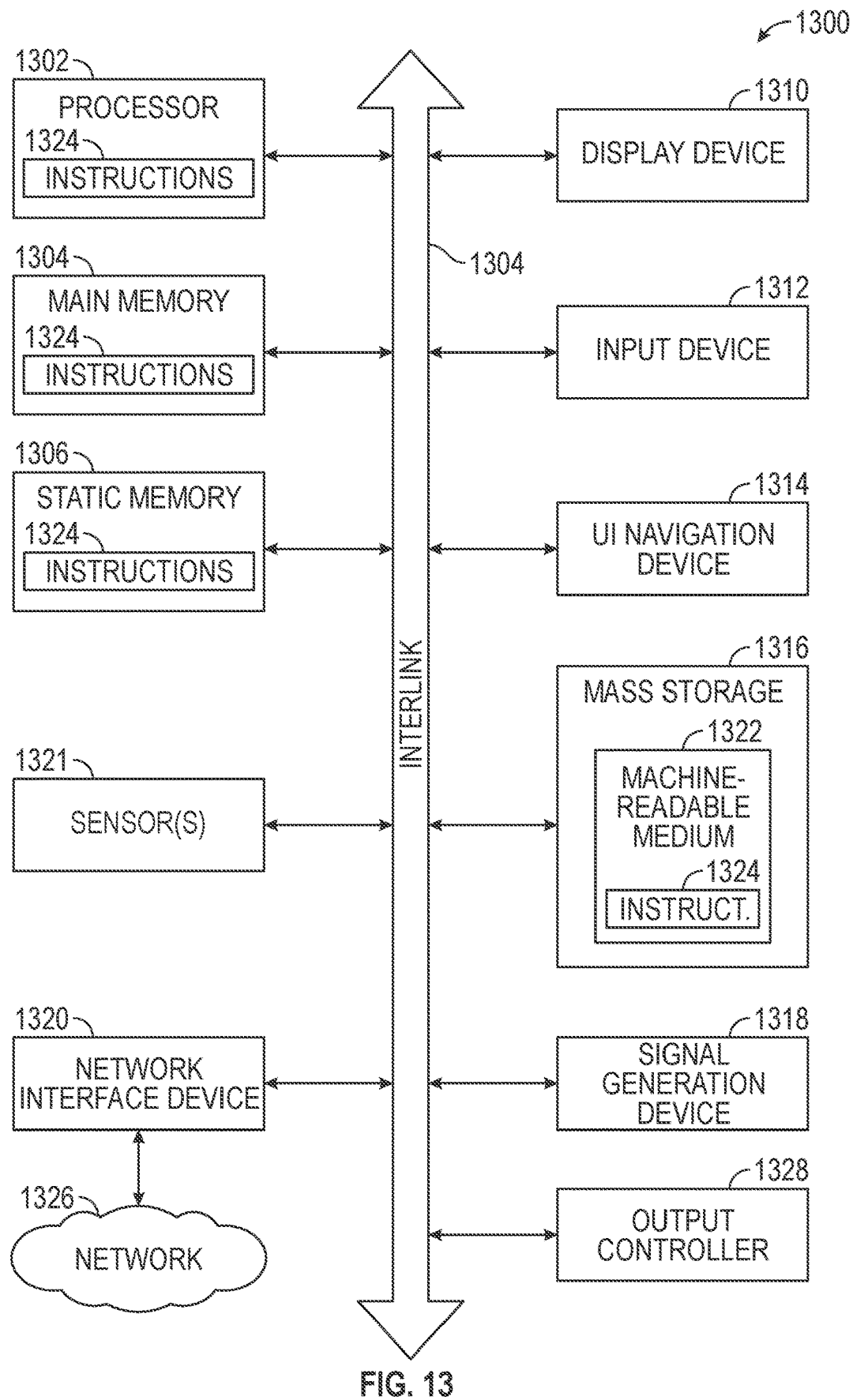
FIG. 13 illustrates a block diagram of an example machine upon which any one or more of the techniques (e.g., methodologies) discussed herein may perform.

FIG. 13 illustrates a block diagram of an example machine 1300 upon which any one or more of the techniques (e.g., methodologies) discussed herein may perform. Portions of this description may apply to the computing framework of various portions of the LCP device, the IMD, or the external programmer.

In alternative embodiments, the machine 1300 may operate as a standalone device or may be connected (e.g., networked) to other machines. In a networked deployment, the machine 1300 may operate in the capacity of a server machine, a client machine, or both in server-client network environments. In an example, the machine 1300 may act as a peer machine in peer-to-peer (P2P) (or other distributed) network environment. The machine 1300 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1300 may include a hardware processor 1302 (e.g., a central processing unit (CPU), a graphics processing unit (GPU), a hardware processor core, or any combination thereof), a main memory 1304 and a static memory 1306, some or all of which may communicate with each other via an interlink (e.g., bus) 1308. The machine 1300 may further include a display unit 1310 (e.g., a raster display, vector display, holographic display, etc.), an alphanumeric input device 1312 (e.g., a keyboard), and a user interface (UI) navigation device 1314 (e.g., a mouse). In an example, the display unit 1310, input device 1312 and UI navigation device 1314 may be a touch screen display. The machine 1300 may additionally include a storage device (e.g., drive unit) 1316, a signal generation device 1318 (e.g., a speaker), a network interface device 1320, and one or more sensors 1321, such as a global positioning system (GPS) sensor, compass, accelerometer, or other sensor. The machine 1300 may include an output controller 1328, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1316 may include a machine readable medium 1322 on which is stored one or more sets of data structures or instructions 1324 (e.g., software) embodying or utilized by any one or more of the techniques or functions described herein. The instructions 1324 may also reside, completely or at least partially, within the main memory 1304, within static memory 1306, or within the hardware processor 1302 during execution thereof by the machine 1300. In an example, one or any combination of the hardware processor 1302, the main memory 1304, the static memory 1306, or the storage device 1316 may constitute machine readable media.

While the machine readable medium 1322 is illustrated as a single medium, the term "machine readable medium" may include a single medium or multiple media (e.g., a centralized or distributed database, and/or associated caches and servers) configured to store the one or more instructions 1324.

The term "machine readable medium" may include any medium that is capable of storing, encoding, or carrying instructions for execution by the machine 1300 and that cause the machine 1300 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1324 may further be transmitted or received over a communications network 1326 using a transmission medium via the network interface device 1320 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1320 may include one or more physical jacks (e.g., Ethernet, coaxial, or phone jacks) or one or more antennas to connect to the communications network 1326. In an example, the network interface device 1320 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1300, and includes digital or analog communications signals or other intangible medium to facilitate communication of such software.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
   an atrial fibrillation (AF) detection circuit configured to receive information about a heart over a first period including a number of cardiac intervals, and to discriminate between an AF event and a non-AF event, the AF detection circuit including:
   a first AF detection circuit configured to determine a first AF indication in the first period using the received information about the heart; and
   a second AF detection circuit configured to receive depolarization information about the heart over the first period, to bin the cardiac intervals into separate rate bins using the received depolarization information, and to cluster the received depolarization information,
   wherein the AF detection circuit is configured to discriminate between an AF event and a non-AF event in the first period using the determined first AF indication and the clustered depolarization information, and
   wherein, to cluster the received depolarization information, the second AF detection circuit is configured to group successive rate bins having bin counts greater than a bin threshold and a group bin count greater than a threshold percentage of the number of cardiac intervals over the first period.

2. The system of claim 1, wherein, when the first AF indication is indicative of an AF event in the first period, the second AF detection circuit is configured to cluster the received depolarization information to verify the first AF indication, and
   wherein the AF detection circuit is configured to provide an indication of an AF event in the first period when the first AF indication is indicative of an AF event in the first period and the clustered depolarization information is indicative of an AF event in the first period.

3. The system of claim 1, wherein, when the first AF indication is indicative of a non-AF event over the first period, the second AF detection circuit does not cluster the received depolarization information, and the AF detection circuit is configured to provide an indication of a non-AF event over the first period using only the first AF indication.

4. The system of claim 1, wherein the AF detection circuit is configured to receive information about a ventricle of the heart, wherein the depolarization information includes ventricular depolarization information, and
   wherein the first AF detection circuit is configured to determine a ventricular rate stability over the first period using the ventricular depolarization information, and to determine the first AF indication using the determined ventricular rate stability.

5. The system of claim 1, wherein the AF detection circuit is configured to receive information about a ventricle of the heart, including ventricular depolarizations, over the first period, and
   wherein the first AF detection circuit is configured to determine the first AF indication using V-V intervals between successive ventricular depolarizations over the first period.

6. The system of claim 1, wherein the received depolarization information includes ventricular depolarization information for cardiac intervals in the first period.

7. The system of claim 6, wherein the AF detection circuit is configured to provide an indication of an AF event in the first period when the first AF indication is indicative of an AF event in the first period and the determined number of clusters over the first period is less than or equal to a cluster threshold.

8. The system of claim 7, wherein the number of cardiac intervals includes a positive integer, X, greater than or equal to 100,
   wherein the separate rate bins have respective values at least X/20 beats apart,
   wherein the bin threshold is at least 4% of X,
   wherein the threshold percentage is at least 20% of X, and
   wherein the cluster threshold is less than or equal to 1.

9. A method, comprising:
   receiving information about a heart over a first period including a number of cardiac intervals using an atrial fibrillation (AF) detection circuit;

determining, using a first AF detection circuit, a first AF indication in the first period using the received information about the heart; and when the first AF indication is indicative of an AF event in the first period:

receiving depolarization information about the heart over the first period using a second AF detection circuit;

binning, using the second AF detection circuit, the cardiac intervals into separate rate bins using the received depolarization information;

clustering, using the second AF detection circuit, the received depolarization information, comprising grouping successive rate bins having bin counts greater than a bin threshold and a group bin count greater than a threshold percentage of the number of cardiac intervals over the first period; and discriminating between an AF event and a non-AF event in the first period using the clustered depolarization information.

10. The method of claim 9, including providing an indication of an AF event in the first period using the AF detection circuit when the first AF indication is indicative of an AF event in the first period and the clustered depolarization information is indicative of an AF event in the first period.

11. The method of claim 9, including, when the first AF indication is indicative of a non-AF event over the first period, providing an indication of a non-AF event over the first period using the AF detection circuit.

12. The method of claim 9, wherein receiving information about the heart over the first period includes receiving information about a ventricle of the heart over the first period, wherein receiving depolarization information about the heart over the first period includes receiving a ventricular rate, and the method further including:

determining a ventricular rate stability over the first period using the second AF detection circuit, wherein determining the first AF indication in the first period using the received information about the heart includes using the determined ventricular rate stability.

13. The method of claim 9, wherein receiving information about the heart over the first period includes receiving information about a ventricle of the heart, including ventricular depolarizations, over the first period, and wherein determining the first AF indication in the first period includes using V-V intervals between successive ventricular depolarizations over the first period.

14. The method of claim 9, wherein receiving depolarization information about the heart over the first period includes receiving ventricular depolarization information for cardiac intervals in the first period.

15. The method of claim 14, including:

providing an indication of an AF event in the first period when the first AF indication is indicative of an AF event in the first period and the determined number of clusters over the first period is less than or equal to a cluster threshold.

16. The method of claim 15, wherein the number of cardiac intervals includes a positive integer, X, greater than or equal to 100, wherein the separate rate bins have respective values at least X/20 beats apart, wherein the bin threshold is at least 4% of X, wherein the threshold percentage is at least 20% of X, and wherein the cluster threshold is less than or equal to 1.

17. At least one non-transitory machine-readable medium including instructions that, when performed by a medical device, cause the medical device to:

receive information about a heart over a first period including a number of cardiac intervals;

determine a first atrial fibrillation (AF) indication in the first period using the received information about the heart; and when the first AF indication is indicative of an AF event in the first period:

receive depolarization information about the heart over the first period;

bin the cardiac intervals into separate rate bins using the received depolarization information;

cluster the received depolarization information, including grouping successive rate bins having bin counts greater than a bin threshold and a group bin count greater than a threshold percentage of the number of cardiac intervals over the first period; and discriminate between an AF event and a non-AF event in the first period using the clustered depolarization information.

18. The at least one non-transitory machine-readable medium of claim 17, including instructions that, when performed by the medical device, cause the medical device to:

provide an indication of an AF event in the first period when the first AF indication is indicative of an AF event in the first period and the clustered depolarization information is indicative of an AF event in the first period.

19. The at least one non-transitory machine-readable medium of claim 17, wherein the instructions that, when performed by the medical device, cause the medical device to receive depolarization information about the heart over the first period include instructions to:

receive ventricular depolarization information for cardiac intervals in the first period.

20. The at least one non-transitory machine-readable medium of claim 19, including instructions that, when performed by the medical device, cause the medical device to:

provide an indication of an AF event in the first period when the first AF indication is indicative of an AF event in the first period and the determined number of clusters over the first period is less than or equal to a cluster threshold, wherein the number of cardiac intervals includes a positive integer, X, greater than or equal to 100, wherein the separate rate bins have respective values at least X/20 beats apart, and wherein the bin threshold is at least 4% of X, wherein the threshold percentage is at least 20% of X, and wherein the cluster threshold is less than or equal to 1.

* * * * *